(12) United States Patent
Honeck et al.

(10) Patent No.: US 6,478,777 B1
(45) Date of Patent: Nov. 12, 2002

(54) INTRODUCER SYSTEM FOR MEDICAL ELECTRICAL LEAD

(75) Inventors: Jordon D. Honeck, Rogers, MN (US); Mark T. Marshall, Forest Lake, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/578,977

(22) Filed: May 25, 2000

(51) Int. Cl.[7] ............................................. A61M 5/178
(52) U.S. Cl. ................................. 604/164.01; 606/159
(58) Field of Search ........................... 604/164.01, 523, 604/248; 606/140, 159; 174/103

(56) References Cited

U.S. PATENT DOCUMENTS

| | | |
|---|---|---|
| 4,624,266 A | 11/1986 | Kane |
| 4,646,755 A | 3/1987 | Kane |
| 5,395,349 A * | 3/1995 | Quiachon et al. ........... 604/248 |
| 5,796,044 A * | 8/1998 | Cobian et al. ............... 174/103 |
| 5,897,567 A * | 4/1999 | Ressenmann et al. ....... 606/159 |
| 5,935,122 A * | 8/1999 | Fourkas et al. ............. 604/523 |
| 6,051,003 A * | 4/2000 | Chu et al. ................... 606/140 |
| 6,090,072 A * | 7/2000 | Kratoska et al. ........ 604/164.01 |

FOREIGN PATENT DOCUMENTS

FR   2 724 566   9/1994

* cited by examiner

Primary Examiner—Teresa Walberg
Assistant Examiner—Leonid M Fastovsky
(74) Attorney, Agent, or Firm—Girma Wolde-Michael; Michael C. Soldner

(57) ABSTRACT

An introducer that includes a tubular outer sheath having proximal and distal ends, a tubular inner sheath having proximal and distal ends, rotatably mounted within the outer sheath, and a knob, positioned at the proximal end of the inner sheath, so that the inner sheath is rotatable through the knob. A gripping mechanism is coupled to the distal end of the inner sheath and rotatable with the inner sheath to compressively engage a distal portion of a lead or catheter extending through the inner sheath in response to the rotation of the inner sheath through the knob.

20 Claims, 5 Drawing Sheets

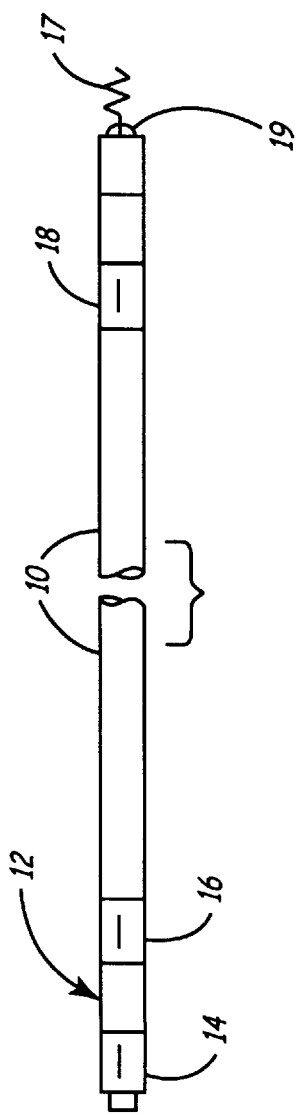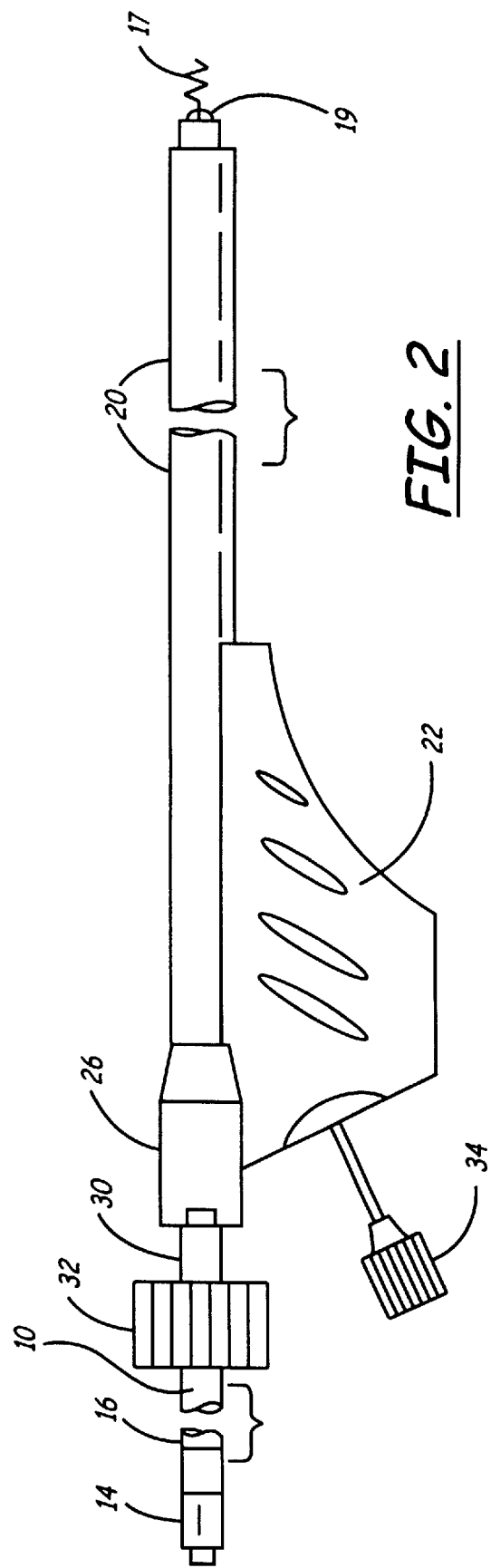

INTRODUCER SYSTEM FOR MEDICAL ELECTRICAL LEAD

BACKGROUND OF THE INVENTION

The present invention relates to indwelling catheters and electrode leads generally and more particularly to introducer systems for directing the placement or removal of fixed-screw catheters and electrode leads in a desired portion of a patient's body.

Catheters and leads may be placed in a desired location in a patient's body, particularly within the patient's vasculature, by means of introducers, guide catheters or introducer catheters, hereafter referred to collectively as "introducers". These introducers typically include an elongated sheath, which is inserted into the blood vessel or other portion of the patient's body, through which the lead or catheter is introduced. Recently, in conjunction with the development of smaller diameter cardiac pacing leads, there has been an increased level of interest in the use of introducers for lead placement. One type of pacing lead which has been proposed for placement by means of an introducer is the small diameter screw-in lead.

Small diameter screw-in leads have several desirable attributes, which are fully disclosed in U.S. Pat. No. 5,246,014, issued to Williams et al. Small-diameter leads, particularly those lacking an internal stylet or other torque transmitting member, tend to have little torsional rigidity and are difficult to screw into tissue using torque applied to the proximal end of the lead body. For such leads, as disclosed in the '014 patent, it has been proposed to provide a mechanism that can impart the rotational torque needed to advance the fixation helix directly to the distal end of the lead body. In the '014 patent, this mechanism takes the form of a tubular member which is adapted to engage the distal end of the lead body and which is rotatable within an associated introducer sheath. In the system disclosed in the '014 patent, the lead was provided with a non-circular cross section at its distal tip, which engaged with a correspondingly formed recess at the distal end of the tubular member. Similar mechanisms have been proposed for introduction of fetal scalp electrodes, as disclosed in U.S. Pat. No. 3,827,428 issued to Hon et al.

SUMMARY OF THE INVENTION

The present invention provides an introducer or guide catheter system that may be used to correctly position a lead having a fixation helix rigidly mounted to the distal end of the lead body (fixed-screw lead) and rotate the fixation helix into body tissue. The introducer system may also be employed to introduce other types of leads or catheters into a patient's body. If desired, the introducer may be used to extract leads as well.

In the preferred embodiments disclosed herein, the introducer includes flexible, tubular inner and outer sheaths. The inner sheath is configured to rotate within the outer sheath and serves as a tool for rotating the distal end of the lead and the fixation helix. The distal portion of the inner sheath is provided with a mechanism for gripping the distal portion of the lead body. The flexible outer sheath in a preferred embodiment is provided with a stylet lumen, in which stylets of pre-set curvatures or deflectable stylets may be inserted, in order to induce desired curvatures in the introducer system.

Unlike the system disclosed in the above-cited '014 patent, the gripping mechanisms of the present invention may be used with leads having a circular cross section at their distal extremities. This capability of the gripping mechanisms allows the use of leads having smooth, iso-diametric profiles over their distal portions. In addition, this feature allows the inner sheath to grip the lead body at multiple locations proximal to the distal end of the lead, so that the distal end of the introducer system need not always be placed immediately adjacent the site at which location of the fixation helix is desired. A knob is attached to the proximal end of the inner sheath, enabling the physician to manipulate the gripping mechanism and screw the fixation helix into tissue and/or remove it from tissue.

In one embodiment of the invention, a filament braid serves as the gripping mechanism. In this embodiment, the physician pulls on the braid from the proximal (knob) end of the introducer to compress the braid around a distal portion of the lead body and thus grip the lead. The inner sheath and the braid are then rotated together to rotate the fixation helix. Alternative gripping mechanism embodiments include a coil and a wound cable, both of which when stretched contract to grip the distal portion of the lead body, and a wedge collett, which collapses to grip the distal portion of the lead body.

The inner sheath and gripping mechanisms of the present invention provide 1:1 torque transfer to the distal end of the lead, allowing easier fixation and/or detachment of the lead for repositioning. The introducer of the present invention may be used to position or remove fixed-screw leads used with bradycardia pacemakers, antitachyarrhythmia devices, or muscle or nerve stimulators. It is particularly beneficial for use in the placement or removal of fixed-screw transvenous leads or catheters with small diameter bodies and little or no torsional rigidity. It may, of course, also be used to position or extract other types of catheters in procedures in which the ability to precisely control rotation of the distal portion of the catheter is desirable.

BRIEF DESCRIPTION OF THE DRAWINGS

FIG. 1 provides a view of an endocardial lead with a screw-in fixation helix. It represents one type of lead that may be introduced with the present invention.

FIG. 2 provides a plan view of an introducer according to the present invention.

FIG. 5b provides a cross-sectional through the distal portion of the sheath of the introducer as in FIG. 5a.

DETAILED DESCRIPTION OF THE PREFERRED EMBODIMENTS

Figure 3:
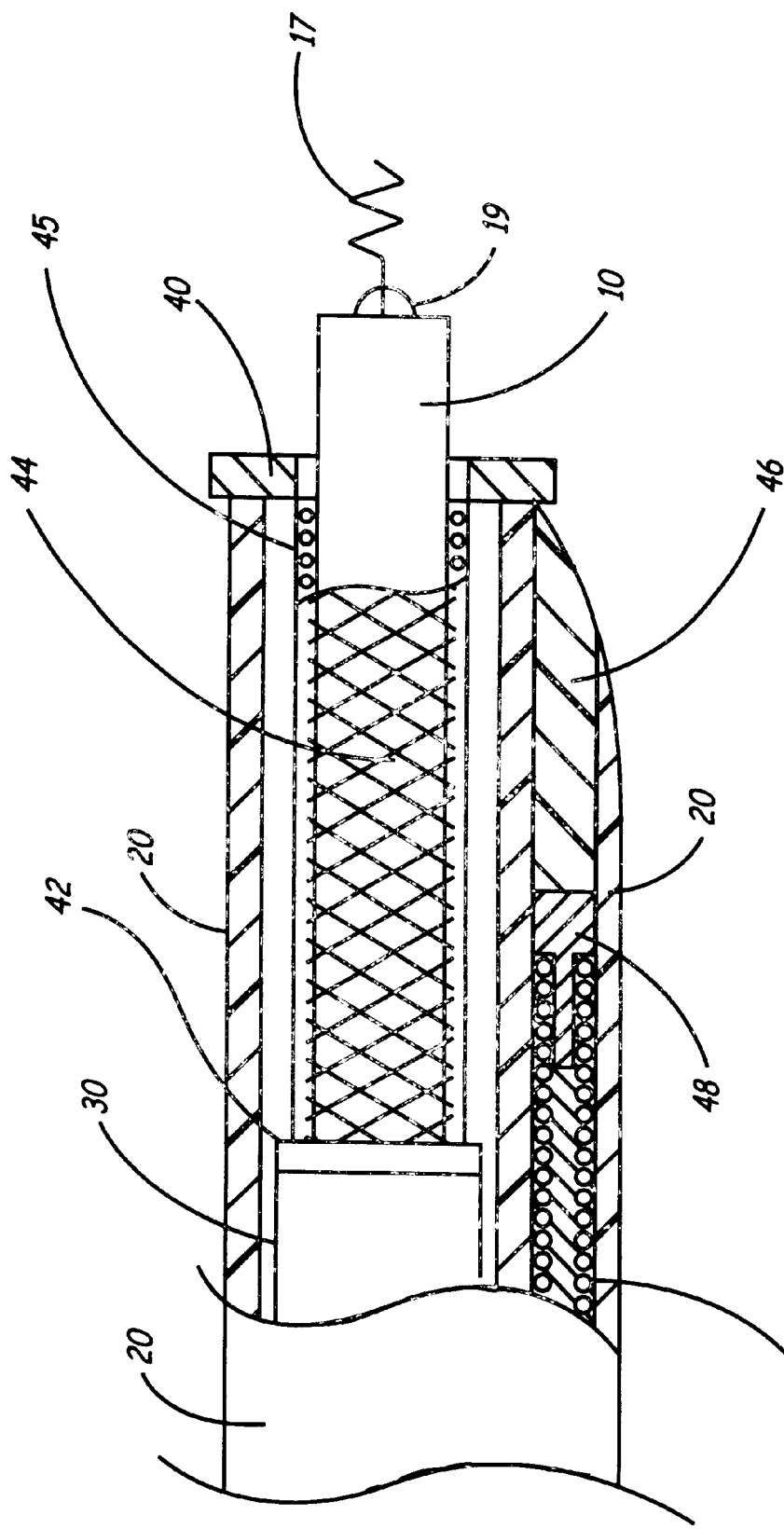
FIG. 3 is an enlarged sectional view through the distal end of a first embodiment of an introducer as generally shown in FIG. 2.

FIG. 1 shows an endocardial pacing lead of a type that may be placed by means of an introducer according to the present invention. The lead is provided with an elongated lead body 10 of circular, generally iso-diametric cross section. The lead is provided with a fixation helix 17, fixedly mounted to the distal end of the lead body 10, employed to anchor the distal end of the lead body to heart tissue. The fixation helix is screwed into heart tissue by rotation of the lead body 10, and may either serve as a pacing or sensing electrode or may serve to anchor a separate electrode, for example as illustrated at 19. Additional electrodes, for example a ring electrode, as illustrated at 18 and/or a physiologic sensor, may also be included. The proximal end of lead body 10 carries a connector assembly 12 which includes one or more connectors 14, 16, each coupled to an electrode or a sensor, if provided, by means of mutually insulated conductors extending within lead body 10.

FIG. 2 is a plan view of an introducer according to the present invention. A pacing lead as in FIG. 1 is illustrated as inserted into the introducer with its distal end, including fixation helix and electrode 19 visible extending distally from the distal end of the introducer and the proximal end of the lead, including connectors 14 and 16, extending proximally from the proximal end of the introducer.

The introducer is provided with an elongated introducer body including flexible, coaxially arranged outer and inner sheaths. The outer sheath 20, which is used to position the lead in the patient's body, may be constructed of conventional biocompatible materials, such as polyether block amide plastic the inner sheath 30 is constructed of a similar material and rotates freely within the outer sheath 20 and is provided with a mechanism at its distal end for gripping the distal portion of the lead. A knob 32 is attached to the proximal end of the introducer and provides the torque necessary to rotate the inner sheath 30 lead body and screw the fixation helix 17 into the tissue. The knob may be constructed of an appropriate metal or plastic.

The handle 22 of the introducer includes a slittable luer fitting 26 that allows removal of the sheath over leads or catheters with large diameter fittings or connectors. As described in co-pending, commonly assigned U.S. patent application Ser. No. 09/116,628, filed Jul. 16, 1998 by Gardeski et al, incorporated herein by reference in its entirety, the luer hub is specifically adapted to be slit using a conventional catheter slitter, which may also be employed to slit the introducer sheaths in some embodiments of the present invention. As illustrated and as described in the Gardeski, et al application, stylet 34 is insertable into the introducer to modify its configuration.

FIG. 3 is a side, cut-away view of an introducer as generally shown in FIG. 2, illustrating a first embodiment of a gripping mechanism according to the present invention. The gripping mechanism includes a tubular braid, which is illustrated at 44 and may be constructed of a standard biocompatible material such as stainless steel, polyester, polyimide, or other metal or plastic. The braid is coupled to the distal end of the inner sheath 30 and is optionally embedded in a tubular elastic polymeric matrix 45 to prevent snagging of the fixation helix on the braid. Matrix 45 is fabricated of a biocompatible material, here illustrated as a clear silicone rubber, through which braid 44 is visible. An optional indicator ring 42 is shown at the distal end of inner sheath 30. At its distal end, the braid 44 is coupled to tip ring 40, which, like braid 44 and inner sheath 30, rotates freely with respect to outer sheath 20. Rings 40 and 42 may be constructed of conventional material such as rigid polyurethane or stainless metal and optionally coated with a radiopaque substance, such as platinum, iridium, gold or tantalum, to allow visualization under fluoroscopy. Optionally, a conductor might be coupled to tip ring 40, allowing it to be used for mapping purposes. As described in the above cited Gardeski, et al application, outer sheath 20 is, in this embodiment, a two-lumen tube, with coil 50, stylet stop 48 and plug 46 located in the second lumen. A deflectable stylet or stylets of selected straight and curved configurations may be inserted into coil 50 to modify the curvature of the introducer body.

When the inner sheath is pulled from the proximal (knob) end of the introducer, the braid is, in turn, pulled axially over the distal portion of the lead body 19, compressing and thus gripping that portion of the lead body 10 located therein. Knob 32 may then be employed to rotate inner sheath 30 and lead body 10 to advance the helix 17 into cardiac tissue or to unscrew the helix from cardiac tissue. Because the gripping mechanism can engage the lead body along the entirety of the distal portion of the lead body 10, the introducer need not extend all the way to the distal end of the lead body.

Figure 4:
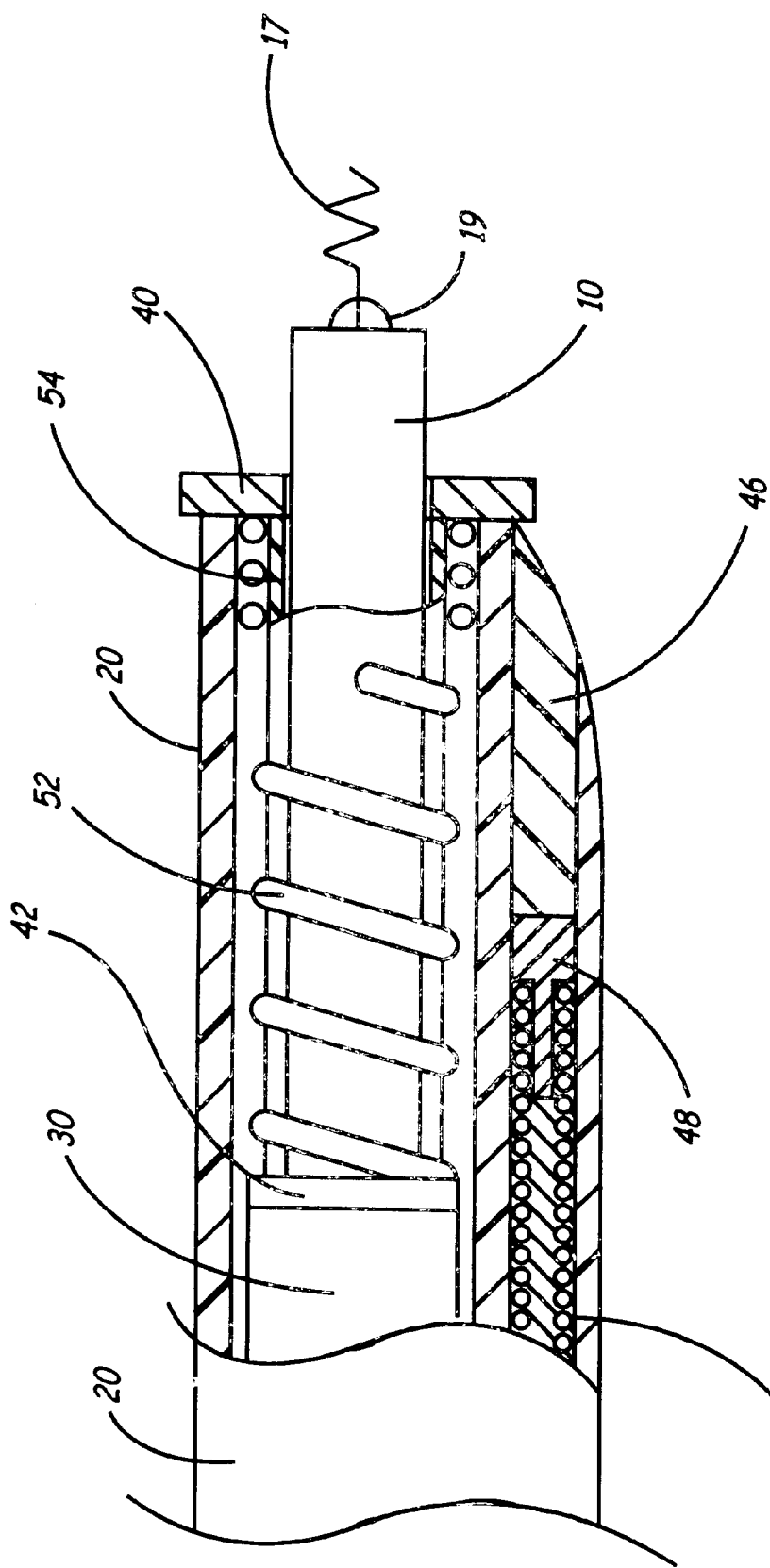
FIG. 4 is an enlarged sectional view through the distal end of a second embodiment of an introducer as generally shown in FIG. 2.

FIG. 4 is a side, cut-away view of an introducer as generally shown in FIG. 2, illustrating a second embodiment of a gripping mechanism according to the present invention. In this embodiment, coil 52 serves as the gripping mechanism. The coil may be constructed of same materials as the braid 44 of FIG. 3 and is likewise coupled to the distal end of the inner sheath 30 and to the rotatable tip ring 40. An optional inner polymeric sleeve 54 may be provided, likewise coupled to one or both of inner sheath 30 and to the rotatable tip ring 40. An optional inner polymeric sleeve 54 may be provided, likewise coupled to one or both of inner sheath 30 and tip ring 40. All other components as illustrated correspond to identically numbered components in FIG. 3. When the inner sheath 30 is rotated clockwise from the proximal knob end of the introducer, the coil 52 contracts to grip the distal portion of the lead body 10. Continued clockwise rotation of the inner sheath allows advancement of the helix 17 into tissue. Alternatively, the inner sheath 30 may be positioned over a lead that is already embedded in tissue. When the inner sheath is rotated counter clockwise from the proximal knob end of the introducer, coil 52 contracts to grip the distal portion of the lead body 10. When the counter clockwise rotation of the inner sheath is continued, the helix will be extracted from the tissue so that the lead body may be removed, or if desired, re-positioned.

Figure 5A:
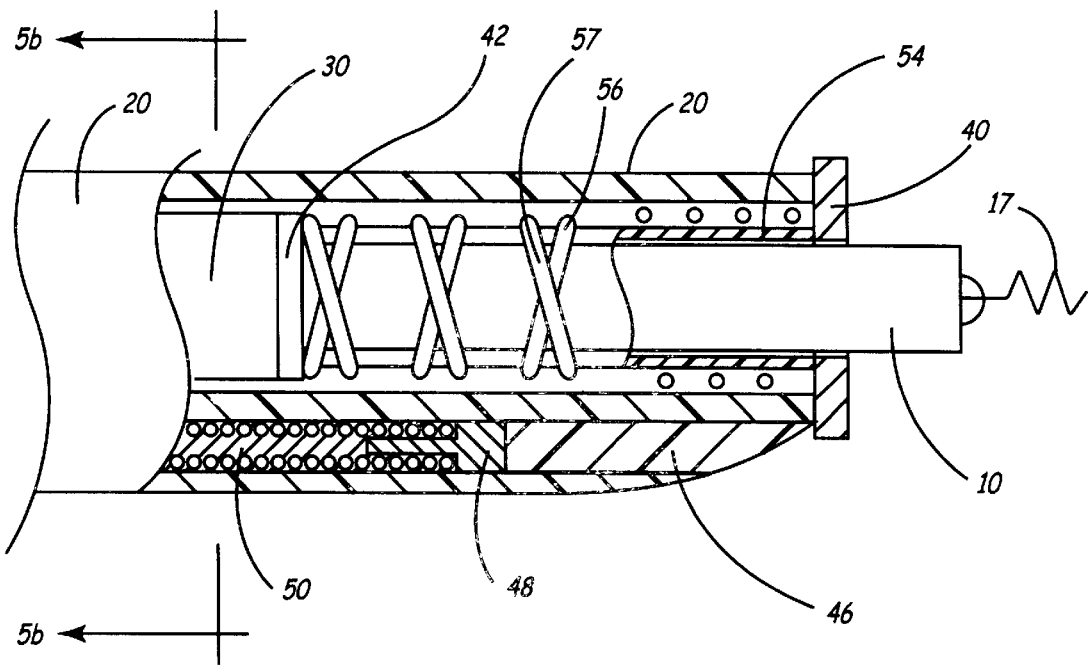
FIG. 5a is an enlarged sectional view through the distal end of a third embodiment of an introducer as generally shown in FIG. 2.
Figure 5B:
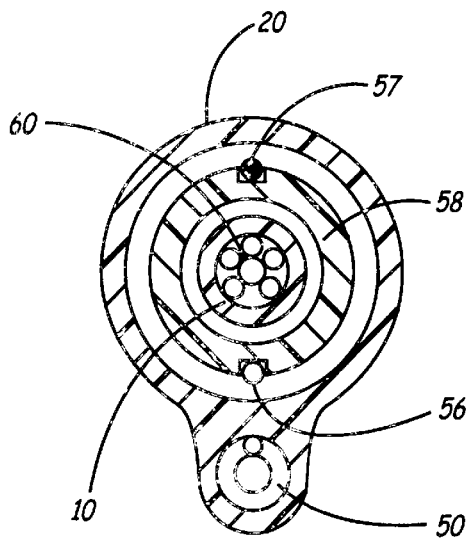

FIG. 5a is a side, cut-away view of an introducer as generally shown in FIG. 2, illustrating a third embodiment of a gripping mechanism according to the present invention. In this embodiment, in which two oppositely wound strands or cables 56 and 57 serve as the gripping mechanism. They may be constructed of same materials as the braid 44 of FIG. 3 and are coupled to rotatable tip ring 40. An optional inner polymeric sleeve 58 may be provided, coupled to one or both of inner sheath 30 and tip ring 40. All other components as illustrated correspond identically numbered components in FIG. 3. The cables 56 and 57 may run the length of the inner sheath 30 and extend to the knob 32 (FIG. 2) at the proximal end of the introducer, as shown in FIG. 5b, or may be directly coupled to the distal end of inner sheath 30. A user pulls proximally on knob 32 to allow the cables to grip the lead body 10. The knob 32 and the inner sheath 30 may then be rotated within the outer sheath 20 to advance the fixation helix 17 into tissue, or alternatively, to remove the helix from the tissue.

FIG. 5b is a cross-sectional view through the distal portion of the introducer of FIG. 5a. In this view, the arrangement of the cables or strands 56, 57 extending along oppositely located slots in inner sheath 10, is visible. The stranded conductor 60 within lead body 10 is also displayed. All other components as illustrated correspond to identically numbered components in FIG. 5a.

Figure 6:
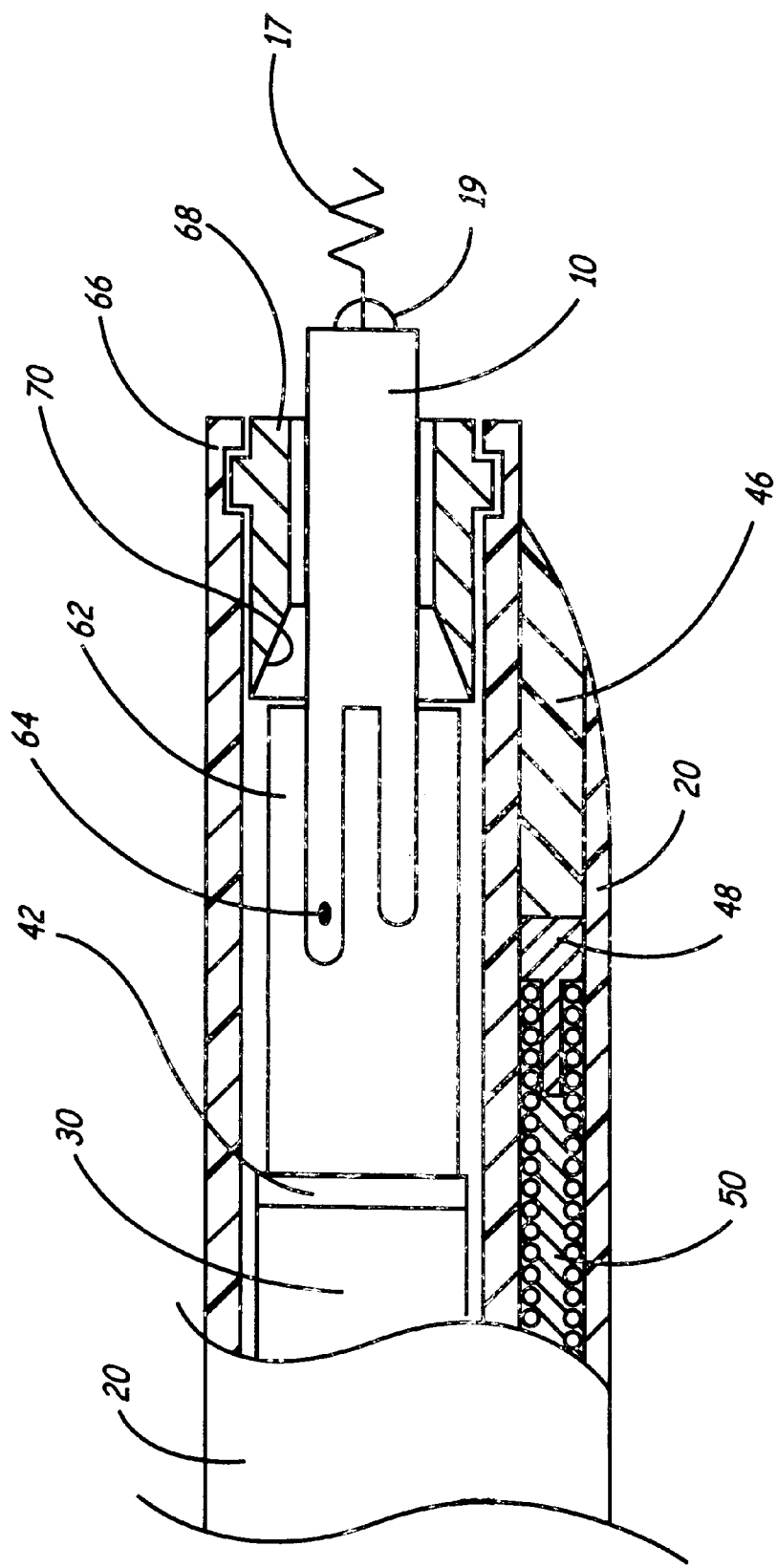
FIG. 6 is an enlarged sectional view through the distal end of a third embodiment of an introducer as generally shown in FIG. 2.

FIG. 6 is a side, cut-away view of an introducer as generally shown in FIG. 2, illustrating a third embodiment of a gripping mechanism according to the present invention. In this embodiment, a wedge and collett serve as the gripping mechanism. The collett 62 may be constructed of same materials as the braid 44 of FIG. 3 and is attached to the distal end of inner sheath 30 or may be formed as an extension of inner sheath 30. Wedge ring 68 may be formed of biocompatible metals or plastics and is rotatably mounted to outer sheath 20 by means of retainer 66. When the inner sheath 30 is pushed from the proximal (knob) end of the introducer, the ramped surface 70 of the wedge ring 68 causes the collett 62 to collapse around and to grip the distal portion of the lead body 10. The widths of slots 64 limit the degree of compression and prevent damage to the lead body 10. Rotation of the inner sheath 30 by means of knob 32 allows advancement of the helix 17 into body tissue or retraction of helix 17 from body tissue.

In conjunction with the above disclosure, we claim:

1. An introducer, comprising:
    a tubular outer sheath having proximal and distal ends;
    a tubular inner sheath having proximal and distal ends, rotatably mounted within the outer sheath;
    a knob, positioned at the proximal end of the inner sheath, the inner sheath being rotatable through the knob; and
    a gripping mechanism coupled to the distal end of the inner sheath and rotatable with the inner sheath, the gripping mechanism comprising means for compressively engaging a distal portion of a lead or catheter extending through the inner sheath in response to the rotation of the inner sheath through the knob.

2. The introducer of claim 1 wherein the gripping mechanism comprises a tubular braid.

3. The introducer of claim 2 wherein the inner sheath is slideable proximally within the outer sheath and wherein the tubular braid is rotatable relative to the outer sheath and coupled to a distal portion of the outer sheath.

4. The introducer of claim 3 wherein the tubular braid is coupled to the distal end of the outer sheath by means of a ring member rotatably mounted at the distal end of the outer sheath.

5. The introducer of claim 1 wherein the gripping mechanism comprises a helical coil.

6. The introducer of claim 5 wherein the inner sheath is slideable proximally within the outer sheath and wherein the helical coil is rotatable relative to the outer sheath and coupled to a distal portion of the outer sheath.

7. The introducer of claim 6 wherein the helical coil is coupled to the distal end of the outer sheath by means of a ring member rotatably mounted at the distal end of the outer sheath.

8. The introducer of claim 1 wherein the gripping mechanism comprises a helically wound strand.

9. The introducer of claim 8 wherein the helically wound strand is rotatable relative to the outer sheath and coupled to a distal portion of the outer sheath.

10. The introducer of claim 9 wherein the helically wound strand is coupled to the distal end of the outer sheath by means of a ring member rotatably mounted at the distal end of the outer sheath.

11. The introducer of claim 8 or claim 9 or claim 10 wherein the gripping mechanism comprises two oppositely wound helical strands.

12. The introducer of claim 1 wherein the gripping mechanism comprises a ramped member and a slidable collett to engage the ramped member.

13. The introducer of claim 12 wherein the inner sheath is slideable distally within the outer sheath and wherein the collett is rotatable relative to the outer sheath and the ramped member is located distal to the collett.

14. The introducer of claim 13, wherein the ramped member is a ring member rotatably mounted at the distal end of the outer sheath.

15. The introducer of claim 2 wherein the tubular braid is embedded in a polymeric matrix.

16. The introducer of claim 1 wherein the outer sheath is a multi-lumen tube.

17. The introducer of claim 16, and further includes a stylet inserted into one of the lumens of the outer sheath.

18. The introducer of claim 17 wherein the stylet has a curved configuration to modify the curvature of the introducer.

19. The introducer of claim 1, and further including an inner polymeric sleeve coupled to the inner sheath.

20. The introducer of claim 1 wherein the gripping mechanism includes slittable luer fitting.

* * * * *